United States Patent [19]
Kotani et al.

[11] Patent Number: 5,026,645
[45] Date of Patent: Jun. 25, 1991

[54] RNA POLYMERASE GENE, MICROORGANISM HAVING SAID GENE AND THE PRODUCTION OF RNA POLYMERASE BY THE USE OF SAID MICROORGANISM

[75] Inventors: Hirokazu Kotani; Nobutsugu Hiraoka, both of Muko; Akira Obayashi, Uji, all of Japan

[73] Assignee: Takara Shuzo Co., Ltd., Kyoto, Japan

[21] Appl. No.: 109,615

[22] Filed: Oct. 19, 1987

[30] Foreign Application Priority Data

Oct. 21, 1986 [JP] Japan .................. 61-248503

[51] Int. Cl.$^5$ .................. C12N 15/00; C12N 9/12; C12N 15/54; C12N 15/70
[52] U.S. Cl. .................. 435/194; 536/27; 435/172.3; 435/69.1; 435/252.33
[58] Field of Search .................. 435/235, 194, 252.3, 435/252.33, 320; 536/27; 932/14, 29, 27, 73

[56] References Cited
PUBLICATIONS

Kassavetis et al., Journal of Billogical Chemistry (1982), vol. 257, No. 10, pp. 5779–5786.
Studier et al., U.S. 6595016 (U.S. Department of Energy) published for exploitation, 8 Oct., 1985.
Kotani et al., Nucleic Acids Research (1987), vol. 15, No. 6, pp. 2653–2664.
Davanloo et al., Proceedings of the National Academy of Sciences (USA) (1984), vol. 81, pp. 2035–2039.
Butler, Journal of Biological Chemistry, vol. 257, No. 10, pp. 5772–5778 (1982).

*Primary Examiner*—Richard A. Schwartz
*Assistant Examiner*—S. L. Nolan
*Attorney, Agent, or Firm*—Wenderoth, Lind & Ponack

[57] ABSTRACT

SP6 bacteriophage RNA polymerase is produced by cultivating a new microorganism (particularly new strains of *Escherichia coli*) harboring a plasmid that carries SP6 bacteriophage RNA polymerase gene and recovering SP6 bacteriophage RNA polymerase from the culture broth. SP6 bacteriophage RNA polymerase gene is provided as are new microorganisms harboring a plasmid that carries SP6 bacteriophage RNA polymerase gene.

3 Claims, 8 Drawing Sheets

FIG. 3(1)

```
                                    GCGCTCAATTAAGTTTTCTAGTACCGCATGAGGATACAAG    -1

1                                    10                                  20
     Met Gln Asp Leu His Ala Ile Gln Leu Gln Leu Glu Glu Glu Met Phe Asn Gly Gly Ile
     ATG CAA GAT TTA CAC GCT ATC CAG CTT CAA TTA GAA GAA GAG ATG TTT AAT GGT GGC ATT    60

30                                  40
     Arg Arg Phe Glu Ala Asp Gln Gln Arg Gln Ile Ala Ala Gly Ser Glu Ser Asp Thr Ala
     CGT CGC TTC GAA GCA GAT CAA CAA CGC CAG ATT GCA GCA GGT AGC GAG AGC GAC ACA GCA    120

50                                  60
     Trp Asn Arg Arg Leu Leu Ser Glu Leu Ile Ala Pro Met Ala Glu Gly Ile Gln Ala Tyr
     TGG AAC CGC CGC CTG TTG TCA GAA CTT ATT GCA CCT ATG GCT GAA GGC ATT CAG GCT TAT    180

70                                  80
     Lys Glu Glu Tyr Glu Gly Lys Lys Gly Arg Ala Pro Arg Ala Leu Ala Phe Leu Gln Cys
     AAA GAA GAG TAC GAA GGT AAG AAA GGT CGT GCA CCT CGC GCA TTG GCT TTC TTA CAA TGT    240

90                                  100
     Val Glu Asn Glu Val Ala Ala Tyr Ile Thr Met Lys Val Val Met Asp Met Leu Asn Thr
     GTA GAA AAT GAA GTT GCA GCA TAC ATC ACT ATG AAA GTT GTT ATG GAT ATG CTG AAT ACG    300

110                                 120
     Asp Ala Thr Leu Gln Ala Ile Ala Met Ser Val Ala Glu Arg Ile Glu Asp Gln Val Arg
     GAT GCT ACC CTT CAG GCT ATT GCA ATG AGT GTA GCA GAA CGC ATT GAA GAC CAA GTG CGC    360

130                                 140
     Phe Ser Lys Leu Glu Gly His Ala Ala Lys Tyr Phe Glu Lys Val Lys Lys Ser Leu Lys
     TTT TCT AAG CTA GAA GGT CAC GCC GCT AAA TAC TTT GAG AAG GTT AAG AAG TCA CTC AAG    420
```

FIG. 3(2)

```
                        150                                        160
Ala Ser Arg Thr Lys Ser Tyr Arg His Ala His Asn Val Ala Val Val Ala Glu Lys Ser
GCT AGC CGT ACT AAG TCA TAT CGT CAC GCT CAT AAC GTA GCT GTA GTT GCT GAA AAA TCA      480

170                                        180
Val Ala Glu Lys Asp Ala Asp Phe Asp Arg Trp Glu Ala Trp Pro Lys Glu Thr Gln Leu
GTT GCA GAA AAG GAC GCG GAC TTT GAC CGT TGG GAG GCG TGG CCA AAA GAA ACT CAA TTG      540

190                                        200
Gln Ile Gly Thr Thr Leu Leu Glu Ile Leu Glu Gly Ser Val Phe Tyr Asn Gly Glu Pro
CAG ATT GGT ACT ACC TTG CTT GAA ATC TTA GAA GGT AGC GTT TTC TAT AAT GGT GAA CCT      600

210                                        220
Val Phe Met Arg Ala Met Arg Thr Tyr Gly Gly Lys Thr Ile Tyr Tyr Leu Gln Thr Ser
GTA TTT ATG CGT GCT ATG CGC ACT TAT GGC GGA AAG ACT ATT TAC TAC TTA CAA ACT TCT      660

230                                        240
Glu Ser Val Gly Gln Trp Ile Ser Ala Phe Lys Glu His Val Ala Gln Leu Ser Pro Ala
GAA AGT GTA GGC CAG TGG ATT AGC GCA TTC AAA GAG CAC GTA GCG CAA TTA AGC CCA GCT      720

250                                        260
Tyr Ala Pro Cys Val Ile Pro Pro Arg Pro Trp Arg Thr Pro Phe Asn Gly Gly Phe His
TAT GCC CCT TGC GTA ATC CCT CCT CGT CCT TGG AGA ACT CCA TTT AAT GGA GGG TTC CAT      780

270                                        280
Thr Glu Lys Val Ala Ser Arg Ile Arg Leu Val Lys Gly Asn Arg Glu His Val Arg Lys
ACT GAG AAG GTA GCT AGC CGT ATC CGT CTT GTA AAA GGT AAC CGT GAG CAT GTA CGC AAG      840
```

FIG. 3(3)

```
                    290                                         300
Leu Thr Gln Lys Gln Met Pro Lys Val Tyr Lys Ala Ile Asn Ala Leu Gln Asn Thr Gln
TTG ACT CAA AAG CAA ATG CCA AAG GTT TAT AAG GCT ATC AAC GCA TTA CAA AAT ACA CAA      900

310                                         320
Trp Gln Ile Asn Lys Asp Val Leu Ala Val Ile Glu Glu Val Ile Arg Leu Asp Leu Gly
TGG CAA ATC AAC AAG GAT GTA TTA GCA GTT ATT GAA GAA GTA ATC CGC TTA GAC CTT GGT      960

330                                         340
Tyr Gly Val Pro Ser Phe Lys Pro Leu Ile Asp Lys Glu Asn Lys Pro Ala Asn Pro Val
TAT GGT GTA CCT TCC TTC AAG CCA CTG ATT GAC AAG GAG AAC AAG CCA GCT AAC CCG GTA     1020

350                                         360
Pro Val Glu Phe Gln His Leu Arg Gly Arg Glu Leu Lys Glu Met Leu Ser Pro Glu Gln
CCT GTT GAA TTC CAA CAC CTG CGC GGT CGT GAA CTG AAA GAG ATG CTA TCA CCT GAG CAG     1080

370                                         380
Trp Gln Gln Phe Ile Asn Trp Lys Gly Glu Cys Ala Arg Leu Tyr Thr Ala Glu Thr Lys
TGG CAA CAA TTC ATT AAC TGG AAA GGC GAA TGC GCG CGC CTA TAT ACC GCA GAA ACT AAG     1140

390                                         400
Arg Gly Ser Lys Ser Ala Ala Val Val Arg Met Val Gly Gln Ala Arg Lys Tyr Ser Ala
CGC GGT TCA AAG TCC GCC GCC GTT GTT CGC ATG GTA GGA CAG GCC CGT AAA TAT AGC GCC     1200

410                                         420
Phe Glu Ser Ile Tyr Phe Val Tyr Ala Met Asp Ser Arg Ser Arg Val Tyr Val Gln Ser
TTT GAA TCC ATT TAC TTC GTG TAC GCA ATG GAT AGC CGC AGC CGT GTC TAT GTG CAA TCT     1260
```

FIG. 3(4)

```
                        430                                         440
Ser Thr Leu Ser Pro Gln Ser Asn Asp Leu Gly Lys Ala Leu Leu Arg Phe Thr Glu Gly
AGC ACG CTC TCT CCG CAG TCT AAC GAC TTA GGT AAG GCA TTA CTC CGC TTT ACC GAG GGA    1320

450                                         460
Arg Pro Val Asn Gly Val Glu Ala Leu Lys Trp Phe Cys Ile Asn Gly Ala Asn Leu Trp
CGC CCT GTG AAT GGC GTA GAA GCG CTT AAA TGG TTC TGC ATC AAT GGT GCT AAC CTT TGG    1380

470                                         480
Gly Trp Asp Lys Lys Thr Phe Asp Val Arg Val Ser Asn Val Leu Asp Glu Glu Phe Gln
GGA TGG GAC AAG AAA ACT TTT GAT GTG CGC GTG TCT AAC GTA TTA GAT GAG GAA TTC CAA    1440

490                                         500
Asp Met Cys Arg Asp Ile Ala Ala Asp Pro Leu Thr Phe Thr Gln Trp Ala Lys Ala Asp
GAT ATG TGT CGA GAC ATC GCC GCA GAC CCT CTC ACA TTC ACC CAA TGG GCT AAA GCT GAT    1500

510                                         520
Ala Pro Tyr Glu Phe Leu Ala Trp Cys Phe Glu Tyr Ala Gln Tyr Leu Asp Leu Val Asp
GCA CCT TAT GAA TTC CTC GCT TGG TGC TTT GAG TAT GCT CAA TAC CTT GAT TTG GTG GAT    1560

530                                         540
Glu Gly Arg Ala Asp Glu Phe Arg Thr His Leu Pro Val His Gln Asp Gly Ser Cys Ser
GAA GGA AGG GCC GAC GAA TTC CGC ACT CAC CTA CCA GTA CAT CAG GAC GGG TCT TGT TCA    1620

550                                         560
Gly Ile Gln His Tyr Ser Ala Met Leu Arg Asp Glu Val Gly Ala Lys Ala Val Asn Leu
GGC ATT CAG CAC TAT AGT GCT ATG CTT CGC GAC GAA GTA GGG GCC AAA GCT GTT AAC CTG    1680
```

FIG. 3(5)

```
                    570                                              580
Lys Pro Ser Asp Ala Pro Gln Asp Ile Tyr Gly Ala Val Ala Gln Val Val Ile Lys Lys
AAA CCC TCC GAT GCA CCG CAG GAT ATC TAT GGG GCG GTG GCG CAA GTG GTT ATC AAG AAG    1740

590                                              600
Asn Ala Leu Tyr Met Asp Ala Asp Asp Ala Thr Thr Phe Thr Ser Gly Ser Val Thr Leu
AAT GCG CTA TAT ATG GAT GCG GAC GAT GCA ACC ACG TTT ACT TCT GGT AGC GTC ACG CTG    1800

610                                              620
Ser Gly Thr Glu Leu Arg Ala Met Ala Ser Ala Trp Asp Ser Ile Gly Ile Thr Arg Ser
TCC GGT ACA GAA CTG CGA GCA ATG GCT AGC GCA TGG GAT AGT ATT GGT ATT ACC CGT AGC    1860

630                                              640
Leu Thr Lys Lys Pro Val Met Thr Leu Pro Tyr Gly Ser Thr Arg Leu Thr Cys Arg Glu
TTA ACC AAA AAG CCC GTG ATG ACC TTG CCA TAT GGT TCT ACT CGC TTA ACT TGC CGT GAA    1920

650                                              660
Ser Val Ile Asp Tyr Ile Val Asp Leu Glu Glu Lys Glu Ala Gln Lys Ala Val Ala Glu
TCT GTG ATT GAT TAC ATC GTA GAC TTA GAG GAA AAA GAG GCG CAG AAG GCA GTA GCA GAA    1980

670                                              680
Gly Arg Thr Ala Asn Lys Val His Pro Phe Glu Asp Asp Arg Gln Asp Tyr Leu Thr Pro
GGG CGG ACG GCA AAC AAG GTA CAT CCT TTT GAA GAC GAT CGT CAA GAT TAC TTG ACT CCG    2040

690                                              700
Gly Ala Ala Tyr Asn Tyr Met Thr Ala Leu Ile Trp Pro Ser Ile Ser Glu Val Val Lys
GGC GCA GCT TAC AAC TAC ATG ACG GCA CTA ATC TGG CCT TCT ATT TCT GAA GTA GTT AAG    2100
```

FIG. 3(6)

```
              710                                              720
Ala Pro Ile Val Ala Met Lys Met Ile Arg Gln Leu Ala Arg Phe Ala Ala Lys Arg Asn
GCA CCG ATA GTA GCT ATG AAG ATG ATA CGC CAG CTT GCA CGC TTT GCA GCG AAA CGT AAT    2160

730                                              740
Glu Gly Leu Met Tyr Thr Leu Pro Thr Gly Phe Ile Leu Glu Gln Lys Ile Met Ala Thr
GAA GGC CTG ATG TAC ACC CTG CCT ACT GGC TTC ATC TTA GAA CAG AAG ATC ATG GCA ACC    2220

750                                              760
Glu Met Leu Arg Val Arg Thr Cys Leu Met Gly Asp Ile Lys Met Ser Leu Gln Val Glu
GAG ATG CTA CGC GTG CGT ACC TGT CTG ATG GGT GAT ATC AAG ATG TCC CTT CAG GTT GAA    2280

770                                              780
Thr Asp Ile Val Asp Glu Ala Ala Met Met Gly Ala Ala Ala Pro Asn Phe Val His Gly
ACG GAT ATC GTA GAT GAA GCC GCT ATG ATG GGA GCA GCA GCA CCT AAT TTC GTA CAC GGT    2340

790                                              800
His Asp Ala Ser His Leu Ile Leu Thr Val Cys Glu Leu Val Asp Lys Gly Val Thr Ser
CAT GAC GCA AGT CAC CTT ATC CTT ACC GTA TGT GAA TTG GTA GAC AAG GGC GTA ACT AGT    2400

810                                              820
Ile Ala Val Ile His Asp Ser Phe Gly Thr His Ala Asp Asn Thr Leu Thr Leu Arg Val
ATC GCT GTA ATC CAC GAC TCT TTT GGT ACT CAT GCA GAC AAC ACC CTC ACT CTT AGA GTG    2460

830                                              840
Ala Leu Lys Gly Gln Met Val Ala Met Tyr Ile Asp Gly Asn Ala Leu Gln Lys Leu Leu
GCA CTT AAA GGG CAG ATG GTT GCA ATG TAT ATT GAT GGT AAT GCG CTT CAG AAA CTA CTG    2520
```

FIG. 3(7)

```
                           850                                          860
         Glu Glu His Glu Glu Arg Trp Met Val Asp Thr Gly Ile Glu Val Pro Glu Gln Gly Glu
         GAG GAG CAT GAA GAG CGC TGG ATG GTT GAT ACA GGT ATC GAA GTA CCT GAG CAA GGG GAG    2580

870           874
         Phe Asp Leu Asn Glu Ile Met Asp Ser Glu Tyr Val Phe Ala ***
         TTC GAC CTT AAC GAA ATC ATG GAT TCT GAA TAC GTA TTT GCC TAA TAG AAC AAT AAA TAT    2640

ACA GGT CAG CCT TCG GGC TGG CCT TTT CTT TTA ACT ATT ACC TGT AAC ATT TAA TTA ACA    2700

AGT CCA ACG TGT TGG ACA C                                                          2719
```

RNA POLYMERASE GENE, MICROORGANISM HAVING SAID GENE AND THE PRODUCTION OF RNA POLYMERASE BY THE USE OF SAID MICROORGANISM

This invention relates to a DNA that carries genetic information for the production of SP6 bacteriophage RNA polymerase, to new microorganisms (particularly new strains of *Escherichia coli*) harboring a plasmid into which said DNA has been integrated, and to a process for producing SP6 bacteriophage RNA polymerase by using said new microorganism.

SP6 bacteriophage RNA polymerase was discovered in 1982, and since then its biochemical properties have been investigated. With the recent progress in molecular genetics, there has been an increasing demand for processes to allow synthesis of uniform RNAs in large quantities and to prepare highly radioactive, single-stranded RNA probes to be used in Northern and Southern blotting techniques. Since RNA polymerase produced by bacteriophage SP6, which tends to infect *Salmonella typhimurium*, was found useful for this purpose, development of an advantageous process for manufacturing this RNA polymerase has been hoped for.

A method of Butler et al. is known for the manufacture of SP6 bacteriophage RNA polymerase, in which *Salmonella typhimurium* is subjected to multiple infection with SP6 bacteriophage and the RNA polymerase is recovered from the infected microbial cells [Journal of Biochemistry, 257, 5772 (1982)].

However, the RNA polymerase cannot be obtained in large quantities by this method, because the amount of this enzyme contained in *Salmonella typhimurium* infected with bacteriophage SP6 is rather small and the operations involved are very intricate. On the other hand, nothing is known about isolation of the gene of SP6 bacteriophage RNA polymerase or about the method of cloning it after ligation with various vectors.

The object of this invention is to create new microorganisms (particularly new strains of *Escherichia coli*) harboring a plasmid that carries the SP6 bacteriophage RNA polymerase gene and suitable for industrial production of said RNA polymerase, and to provide a process for producing SP6 bacteriophage RNA polymerase by using said new microorganism.

Briefly, the first aspect of this invention relates to the gene of SP6 bacteriophage RNA polymerase.

The second aspect of this invention relates to new microorganisms harboring a plasmid into which SP6 bacteriophage RNA polymerase gene has been integrated.

The third aspect of this invention relates to a process for producing SP6 bacteriophage RNA polymerase, which comprises cultivating said new microorganism and recovering SP6 bacteriophage RNA polymerase from the culture broth.

We have succeeded in cloning 2.75 kb DNA fragment containing the whole region of SP6 bacteriophage RNA polymerase gene out of bacteriophage SP6 DNA, and found that cultivation of a microorganism, particularly a strain of *Escherichia coli*, into which a plasmid that carries said cloned DNA fragment has been integrated gives a significant quantity of SP6 bacteriophage RNA polymerase accumulated in the grown microbial cells. This invention was accomplished based on these findings.

This invention will be detailed below by referring to the accompanying drawings wherein:

FIG. 3 shows the base sequence of the 2.75 kb DNA described later.

Figure 1:
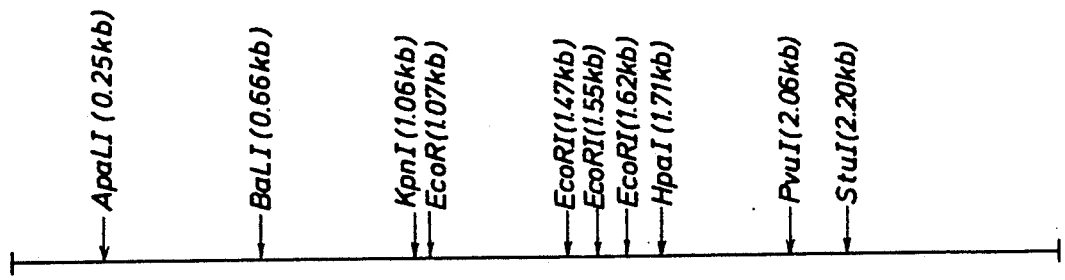
FIG. 1 is a restriction enzyme cleavage map of the 2.75 kb DNA containing SP6 bacteriophage RNA polymerase gene.

The new microorganism (for example, new strain of *Escherichia coli*) may be obtained according to the procedure given below.

(1) Phage DNA, extracted from bacteriophage SP6 (DNA donor), is cleaved with suitable restriction enzymes and a desired DNA fragment is recovered.

(2) The recovered DNA fragment is shortened by digestion at terminals with exonuclease Bal 31.

(3) A plasmid vector is cleaved with suitable restriction enzymes, and the DNA fragment obtained in (2) above is ligated to the cleaved ends of said plasmid.

(4) The plasmid into which the phage DNA fragment has been integrated is then introduced into a host, and a transformant that carries the intended DNA fragment is screened out.

(5) The plasmid is isolated from the transformant obtained in (4) above, and the desired DNA fragment is cut out from the isolated plasmid and ligated to an expression vector plasmid in the same manner as in (3) above.

(6) The expression vector plasmid obtained in (5) above (containing DNA fragment that carries SP6 bacteriophage RNA polymerase gene) is introduced into a host in the same manner as in (4) above.

The bacteriophage SP6 DNA used in the above process as DNA donor can be obtained by infecting *Salmonella typhimurium* LT2 strain with bacteriophage SP6, and recovering phage particles from the lysate thus formed, followed by extraction. Known techniques may be used for extraction, purification and cleavage with restriction enzymes, as detailed on pages 75-178 in "Molecular Cloning, a Laboratory Manual" (published from The Cold Spring Harbor Laboratory in 1982).

Cleavage of phage DNA with a restriction enzyme is carried out as described below. A suitable restriction enzyme is added to the reaction mixtures containing phage DNA, and cleavage reaction is carried out under suitable conditions to produce a number of DNA fragments. The enzyme used must be the one which is capable of cleaving phage DNA and does not cleave the DNA region that carries genetic information for the production of SP6 bacteriophage RNA polymerase. It is also preferable that the restriction enzyme cleaves the vector plasmid only at one site.

Cleavage of the plasmid vector is also effected in a similar way.

Known vector plasmids, for example pBR322, pUC18 and pUC19, may be used for the purpose of this invention. The above-mentioned DNA fragment is then spliced to the plasmid vector at its cleaved site by known techniques. The reaction conditions should be properly selected according to the types of vector DNA and restriction enzyme used.

An exonuclease is used in order to effect digestion at ends of DNA fragment and to give short DNA fragments. A known example is Bal 31 exonuclease, which produces DNA fragments of different lengths under various reaction conditions.

The plasmid carrying phage DNA fragment thus obtained is then introduced into a strain of *Escherichia coli* as host cells. Any type of *Escherichia coli* strain, both native and wild, may be used for this purpose so long as it is capable of transformation. It is also possible that a suitable type of *Escherichia coli* strain is selected depending on the type of vector plasmid used.

Cloning may then be effected depending upon the nature of plasmid vactor used, for example, by screening out ampicilin-resistant and tetracycline-sensitive colonies when pBR322 is employed as plasmid vector and the desired DNA fragment is ligated at its EcoRV site.

Analysis of cloned DNA thus obtained may be done by known methods; the length of cloned DNA fragment can be determined by isolating plasmids from many transformants obtained, followed by cleavage with a suitable restriction enzyme and electrophoresis on agarose gel. It was found that a plasmid carrying a cloned DNA with a length of 2.75 kb (pSP6-1) was actually obtained.

More detailed analysis revealed that this cloned DNA fragment carries SP6 bacteriophage RNA polymerase gene. FIG. 1 shows the restriction enzyme cleavage map of the 2.75 kb DNA carrying SP6 bacteriophage RNA polymerase gene.

The amount of RNA polymerase produced by the *Escherichia coli* strain into which plasmid pSP6-1 (pBR322 with SP6 bacteriophage RNA polymerase gene spliced thereto at its EcoRV site) has been introduced is not so large. It is therefore necessary to use other type of vector plasmid (for example, pUC18) in order to ensure mass production of RNA polymerase. When using pUC18, for example, plasmid pSP6-1 is treated with restriction enzymes, Bam HI and Hind III, to cut out DNA fragment of SP6 bacteriophage RNA polymerase, this fragment is spliced to pUC18 cleaved with Bam HI and Hind III, and the spliced molecule is used for transforming *E. coli* host cells (e.g., JM109 strain). Plasmid pSP6-2 was obtained in this way.

Whether an *E. coli* strain harboring a plasmid into which SP6 bacteriophage RNA polymerase gene has been integrated is producing the RNA polymerase protein or not may be examined by any known method, for example, by the method reported in Journal of Biochemistry, 257, 5772 (1982). When the protein is produced in significant quantities, it can be detected by lysing the microbial cells and subjecting the lysate thus obtained directly to SDS-polyacrylamide gel electrophoresis.

Plasmids carrying SP6 bacteriophage RNA polymerase gene, and *E. coli* strains harboring such a plasmid, can thus be prepared.

The following Examples will further illustrate the invention but are not intended to limit its scope.

EXAMPLE 1

(1) Preparation of bacteriophage SP6 DNA

*Salmonella typhimurium* LT2 strain was grown in 1 liter of modified L medium (containing 10 g/l Bacto-trypton, 5 g/l yeast extract, 5 g/l NaCl, 6 g/l disodium phosphate and 3 g/l monosodium phosphate) at 40° C. When the cell density reached $1.6 \times 10^9$ cells/ml, bacteriophage SP6 was added at a multiplicity of 0.05 pfu/cell, and the mixture was incubated at 40° C. until the microbial cells were lysed.

Chloroform (8 ml) was then added, the mixture was incubated for 15 minutes, DNase and RNase (1 mg each) were further added, and the resulting mixture was held at room temperature for 30 minutes. After addition of 29 g sodium chloride, the reaction mixture was allowed to stand at 4° C. for one hour and centrifuged. To 1 liter of the supernatant recovered, was added 60 g of polyethylene glycol #6000, the solution thus obtained was allowed to stand overnight at 4° C., and the resulting mixture was centrifuged, giving SP6 bacteriophage as precipitate. It was dissolved in 6 ml of B-A buffer [containing 0.5% Nonidet P40 (Shell Oil Co., Ltd.), 3.5 mM $CaCl_2$, 5 mM $MgCl_2$, 30 mM Tris-HCl (pH 7.5), 120 mM KCl, 0.5 mM EDTA and 30 mM 2-mercaptoethanol)]. The solution was overlaid on 3 ml of 40% glycerol buffer [containing 40% glycerol, 0.5% Nonidet P40, 30 mM Tris-HCl (pH 7.5), 120 mM KCl and 30 mM 2-mercaptoethanol)] placed in a centrifuge tube, and subjected to ultracentrifugation at 4° C. (35000 rpm, 1 hour), thus recovering SP6 bacteriophage as precipitate. It was dissolved in 5 ml of Lysis buffer [containing 40 mM Tris-HCl (pH 8.0), 10 mM EDTA, 2% SDS and 100 μg/ml proteinase K], and the solution was held at 55° C. for one hour to complete the reaction.

To the reaction mixture thus obtained, was added an equal amount of a phenol solution [containing 10 mM Tris-HCl (pH 8.0) and phenol saturated with 1 mM EDTA], the mixture was gently stirred and then subjected to centrifugal separation, and the aqueous layer was collected (this operation is hereinafter referred to as "phenol treatment"). To this aqueous solution, was added twice its volume of ethanol, and the mixture was held at −70° C. for 30 minutes, thus giving, as precipitate, SP6 bacteriophage DNA (this operation is hereinafter referred to as "ethanol precipitation"). After removal of ethanol, the precipitate was dissolved in TE solution [containing 10 mM Tris-HCl (pH 8.0) and 1 mM EDTA)] to be ready for use in the next step.

(2) Preparation of restriction-enzyme cleavage map for SP6 bacteriophage DNA

Bacteriophage SP6 DNA (2 μg) obtained in (1) above was treated with 5 U of Hind III under optimum conditions [10 mM Tris-HCl (pH 7.5), 7 mM $MgCl_2$, 60 mM NaCl] at 37° C. for one hour, and the reaction mixture was analyzed by electrophoresis on 1% agarose gel. The restriction enzyme cleavage map thus obtained is shown in FIG. 2, in which A∼N are DNA fragments cut out by Hind III.

(3) Analysis of the region similar to T7 RNA polymerase

Figure 2:
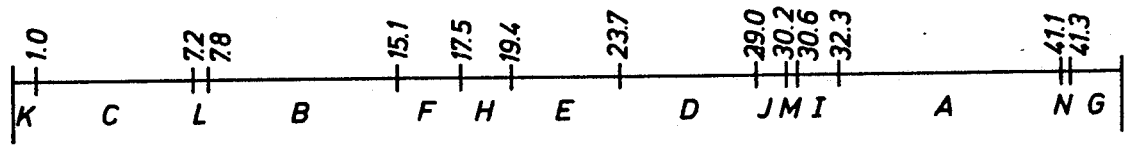
FIG. 2 is the Hind III cleavage map of SP6 bacteriophage DNA.

The cleavage map shown in FIG. 2, the report by Kassavetis et al. [Journal of Biochemistry, 257, 5779 (1982)] and that by Stahl et al. [Journal of Molecular Biology, 148, 481 (1981)] suggested the possibility that information about RNA polymerase gene might be coded in the Hind III-C fragment (6.2 kb). Hence, it was attempted to determine part of the DNA sequence and convert it into amino acid sequence, thereby checking its similarity to T7 RNA polymerase.

SP6 DNA (100 μg) was cleaved with 300 U of Hind III. The resulting mixture was subjected to electrophoresis on 1% agarose gel, and the portion of gel containing 6.2 kb Hind III-C fragment was cut out. The cut out gel was put in a centrifuge tube and eluted into a buffer solution through electrophoresis, and the DNA was recovered from the eluate by addition of ethanol.

The DNA fragment thus obtained was then cleaved with restriction enzymes, Kpn I and Sau 3AI, and sequencing was done as described below according to the dideoxy method of Messing et al. [Method in Enzymology, 101, 20 (1983)]. The fragments obtained by celavage with Kpn I and Sau 3AI were spliced to M13 mp 18 vector at its Bam HI and Kpn sites, and the reconstituted molecule was used for transformation of *E. coli* JM109. The phage plaque thus obtained was grown in 1.5 ml of 2YT medium (containing 16 g/l Bacto. trypton, 8 g/l yeast extract and 5 g/l sodium chloride; pH 7.2), the single stranded DNA was recovered, and its sequence was determined (about 100 bp). After conversion into amino acid sequence, it was compared with that of T7 RNA polymerase, and high similarity was observed between the two. This indicates that the genetic information about SP6 bacteriophage RNA polymerase is coded in DNA fragment of about 2.75 kb containing the Kpn I site.

(4) Cloning of 2.75 kb DNA fragment containing SP6 bacteriophage RNA polymerase gene Hind III-C DNA fragment obtained in (3) above (30 μg) was treated with restriction enzymes, Dra I (100 U) and Bbi II (100 U), in a buffer solution [Tris-HCl (pH 7.4), 5 mM $HgCl_2$, 7 mM 2-mercaptoethanol and 0.01% BSA] at 30° C. for two hours to effect cleavage reaction. The DNA fragments thus obtained were separated by electrophoresis on 1% agarose gel, recovering 10 μg of 3.4 kb DNA fragment (D-B DNA fragment) in the same manner as in (3) above.

This D-B DNA fragment (5 μg) was then treated with 5 U of exonuclease Bal 31 in Bal buffer [20 mM Tris-HCl (pH 8.0), 12 mM $CaCl_2$, 12 mM $MgCl_2$, 1 mM EDTA and 600 mM NaCl] at 20° C. for five minutes. After the reaction was terminated by adding 10 μl of 0.5M EDTA, DNA (Bal DNA fragment) was recovered by phenol treatment, followed by ethanol precipitation.

pBR322 (2 μg) was used as the vector. It was treated with 5 U of restriction enzyme Eco RV in a buffer solution [10 mM Tris-HCl (pH 7.5), 7 mM $MgCl_2$, 150 mM NaCl, 7 mM 2-mercaptoethanol and 0.01% BSA] at 37° C. for one hour, the enzyme was inactivated by heating the reaction mixture at 65° C. for ten minutes, and DNA was recovered by ethanol precipitation. It was dissolved in BAP buffer [100 mM Tris-HCl (pH 8.0)], 1 U of alkaline phosphatase was added, and the reaction was continued at 5° C. for 30 minutes. Vector DNA was recovered from the reaction mixture by phenol treatment, followed by ethanol precipitation.

Bal DNA fragment (0.1 μg) was ligated to pBR322 cleaved with Eco RV (0.15 μg) by treating the mixture of the two with 100 U of T4 DNA ligase in a buffer solution [Tris-HCl (pH 7.6), 6.6 mM $MgCl_2$, 10 mM DTT and 0.5 mM ATP] at 16° C. for four hours.

*Escherichia coli* HB101 strain was grown in 5 ml of L medium (containing 10 g/l Bacto. trypton, 5 g/l yeast extract and 5 g/l sodium chloride; pH 7.2) at 37° C. for 16 hours. The master culture thus obtained (0.1 ml) was inoculated to 5 ml of fresh L medium, and shake culture was continued until OD (optical density) at 600 nm reached 0.6. The preculture thus obtained (2.5 ml) was ice-cooled and centrifuged at 3000 rpm for ten minutes. After complete removal of the supernatant, the residue was mixed well with 1.25 ml of ice-cooled 0.1M solution of $CaCl_2$, and the resulting homogeneous mixture was held in ice water for 30 minutes and again subjected to centrifugation to remove the supernatant. To the residue thus separated, was added 10 μl of the DNA solution prepared above by ligation of Bal DNA fragment to pBR322, and the mixture was held in ice water for 30 minutes. It was then heated at 42° C. for 90 seconds, 2 ml of L medium was added, and the resulting mixture was held at 37° C. for 30 minutes.

The culture broth thus obtained was plated on L-agar medium containing 50 μg/ml ampicillin, and colonies grown at 37° C. were collected. These were replicated on L-agar medium comtaining 15 μg/ml tetracycline, those colonies which failed to grow were collected, and the plasmid involved was analyzed as described below.

The ampicilin-resistant and tetracycline-sensitive strain thus obtained was cultivated in 5 ml of L medium containing 50 μg/ml ampicillin at 37° C. for 16 hours, the grown cells were collected, 0.2 ml of Solution I [50 mM glucose, 10 mM Tris-HCl (pH 8.0), 5 mM EDTA and 2 mg/ml lysozyme)] was added, and the mixture was held in ice water for 30 minutes. Then added was 0.4 ml of Solution II (0.2N NaOH and 1% SDS), followed by addition of 0.3 ml Solution III [3M sodium acetate (pH 4.8)] five minutes later, and the mixture was held at 0° C. for 30 minutes and cenrtrifuged. The supernatant was collected, ethanol was added, the precipitate which separated out was dissolved in 0.2 ml of Solution IV [25 mM Tris-HCl (pH 8.5), 1 mM EDTA, 150 mM NaCl and 1 mg/ml RNase A], and the resulting solution was held at 37° C. for 30 minutes. At the end of reaction, 0.2 ml of Solution V (20% polyethylene glycol #6000 and 2M NaCl) was added, and the mixture was held at −20° C. for 30 minutes.

The precipitate, collected by centrifugation, was dissolved in TE solution, and plasmid DNAs were recovered by phenol treatment and ethanol precipitation and dissolved in 10 μl of TE solution.

This DNA solution was treated with Bam HI and Hind III, and the sizes of DNA fragments integrated were determined by electrophoresis on agarose gel. It was found that plasmids of various sizes had been obtained (the longest DNA contained being 2.75 kb). The plasmid which contains this 2.75 kb DNA was named pSP6-1. The base sequence of the 2.75 kb DNA is shown in FIG. 3. The *Escherichia coli* strain carrying said plasmid, *Escherichia coli* HB101/pSP6-1, has been deposited at Fermentation Research Institute, the Agency of Industrial Science and Technology of Japan, under FERM BP-1418. This is a plasmid carrying the whole region of SP6 bacteriophage RNA polymerase gene.

(5) Ligation of DNA fragment carrying SP6 bacteriophage RNA polymerase gene to pUC18 and introducing the resulting plasmid into *Escherichia coli*

Palsmid pSP6-1 DNA obtained in (5) above was cleaved with Bam HI and Hind III, and the reaction mixture was subjected to agarose gel electrophoresis, giving 3.1 kbp DNA fragment containing the abovementioned 2.75 kb DNA. Separately, pUC18 DNA was also cleaved with Bam HI and Hind III, and the resulting mixture was treated with alkaline phosphatase in the same maner as in (4) above, giving the intended vector DNA.

The two DNA fragments obtained above were linked together in the same way as above, and the reconstituted molecule was used for transforming *Escherichia coli* JM109 strain (Gene, 33, 103–119, 1985). Analysis of the plasmid contained in the transformant in the same way as in (4) above showed that it contains 3.1 kb DNA fragment, and this plasmid was named pSP6-2.

(6) Production of SP6 bacteriophage RNA polymerase by *Escherichia coli* strain carrying plasmid pSP6-2 (*Escherichia coli* JM109/pSP6-2)

The above-mentioned *E. coli* strain was inoculated to 10 ml of L medium containing 50 μg/ml ampicillin and cultivated at 37° C. for 16 hours. The preculture thus obtained was transferred to 500 ml of L medium placed in a 2-liter flask, and the cells were cultivated at 37° C. for five hours (120 rpm). After adition of 50 mg/ml IPTG (isopropyl-1-thio-β-D-galactopyranoside), cultivation was continued for an additional three hours, and the grown cells were collected and suspended in 15 ml of buffer solution IV [50 mM Tris-HCl (pH 8.0), 10% sucrose and 10 mM 2-mercaptoethanol]. To this suspension, were added 20 μg/ml of PMSF (phenylmethanesulfonyl fluoride) and 2 mg/ml of lysozyme, and the mixture was held in ice water for 30 minutes.

Spermidine (0.12 g) and deoxycholic acid (to a concentration of 0.05%) were then added, and the resulting mixture was stirred for five minutes and subjected to ultracentrifugation (10500×g, 1 hour) to recover the supernatant. Activity measurement revealed 800,000 U SP6 bacteriophage RNA polymerase produced—approximately 30 times higher productivity than the case when *Salmonella typhimurium* LT2 strain was infected with SP6.

As is apparent from the foregoing, SP6 bacteriophage RMA polymerase gene was first isolated in this invention. It was also demonstrated that microorganisms containing a plasmid that carries said gene are capable of effectively producing SP6 bacteriophage RNA polymerase which is of great use in genetic engineering.

The meanings of the various symbols used in FIG. 3 are well known in the art of genetic engineering technology and are defined, for example, in "Chemistry and Biochemistry of the Amino Acids", page 9, Edited by G. C. Barrett, published by Chapman and Hall, 1985.

What we claim is:

1. An isolated gene encoding SP6 bacteriophage RNA polymerase.

2. *Escherichia coli* containing a plasmid which comprises an isolated gene encoding SP6 bacteriophage RNA polymerase.

3. Process for producing SP6 bacteriophage RNA polymerase which comprises cultivating *Escherichia coli* containing a plasmid that carries an isolated SP6 bacteriophage RNA polymerase gene under conditions sufficient to produce the SP6 bacteriophage RNA polymerase and recovering the SP6 bacteriophage RNA polymerase from the culture.

* * * * *